(12) United States Patent
Ikeda

(10) Patent No.: US 8,083,670 B2
(45) Date of Patent: Dec. 27, 2011

(54) ENDOSCOPE WITH AXIALLY DISPLACEABLE BALLOON

(75) Inventor: Toshiyuki Ikeda, Saitama (JP)

(73) Assignee: Fujifilm Corporation, Tokyo (JP)

( * ) Notice: Subject to any disclaimer, the term of this patent is extended or adjusted under 35 U.S.C. 154(b) by 594 days.

(21) Appl. No.: 11/797,850

(22) Filed: May 8, 2007

(65) Prior Publication Data

US 2007/0270645 A1 Nov. 22, 2007

(30) Foreign Application Priority Data

May 17, 2006 (JP) ................................. 2006-137596

(51) Int. Cl.
*A61B 1/00* (2006.01)
(52) U.S. Cl. .................. 600/116; 600/115; 600/129
(58) Field of Classification Search .................. 600/115, 600/116, 121, 127, 129; 604/101.01, 95.03, 604/103.11
See application file for complete search history.

(56) References Cited

U.S. PATENT DOCUMENTS

| | | | | | |
|---|---|---|---|---|---|
| 4,464,175 | A | * | 8/1984 | Altman et al. | 604/99.01 |
| 5,144,848 | A | * | 9/1992 | Uenishi et al. | 73/866.5 |
| 5,152,277 | A | * | 10/1992 | Honda et al. | 600/116 |
| 6,086,528 | A | * | 7/2000 | Adair | 600/104 |
| 6,605,056 | B2 | * | 8/2003 | Eidenschink et al. | 604/96.01 |
| 2002/0151870 | A1 | * | 10/2002 | Grimes et al. | 604/509 |
| 2007/0015966 | A1 | * | 1/2007 | Niwa et al. | 600/115 |
| 2010/0298634 | A1 | * | 11/2010 | Yanuma | 600/104 |

FOREIGN PATENT DOCUMENTS

| | | |
|---|---|---|
| JP | 6-269392 A | 9/1994 |
| JP | 8-117231 A | 5/1996 |
| JP | 10-127564 A | 5/1998 |
| JP | 2005-270335 A | 10/2005 |
| JP | 2005-334475 A | 12/2005 |

OTHER PUBLICATIONS

Machine english translation of JP 2005-270335.*
Machine english translation of JP 2005-334475.*

* cited by examiner

*Primary Examiner* — John P Leubecker
*Assistant Examiner* — Victoria Chen
(74) *Attorney, Agent, or Firm* — Birch, Stewart, Kolasch & Birch, LLP

(57) ABSTRACT

The present invention provides an endoscope comprising: an insertion unit which is to be inserted into a body; and a pipeline provided inside the insertion unit for supplying a fluid to a balloon mounted on an outer peripheral surface of the insertion unit, wherein the pipeline has a plurality of openings in an axial direction of the insertion unit on the outer peripheral surface of the insertion unit. Therefore, the endoscope of the present invention can easily fix a balloon and keep airtightness after the fixation, and can raise a degree of freedom of a mounting location of the balloon.

2 Claims, 6 Drawing Sheets

ENDOSCOPE WITH AXIALLY DISPLACEABLE BALLOON

BACKGROUND OF THE INVENTION

1. Field of the Invention

The present invention relates to an endoscope, and in particular, to an endoscope having an insertion unit that is inserted into deep digestive tracts such as a small intestine and a large intestine to be observed.

2. Description of the Related Art

When an insertion unit of an endoscope is inserted in deep digestive tracts, such as a small intestine, since a force is not easily transmitted to a tip of the insertion unit by merely pushing the insertion unit because of complicated bending of an intestinal tract, it is hard to perform insertion into the depth. For example, when excessive bending or flexion arises in the insertion unit, it becomes impossible to further insert the insertion unit into the depth. Then, a method is proposed, which prevents excessive bending or flexion of an insertion unit by putting an insertion aid on the insertion unit of the endoscope and inserting the insertion unit into a body cavity, and guiding the insertion unit by this insertion aid.

Japanese Patent Application Laid-Open No. 2005-334475 discloses an endoscope apparatus which not only provides a first balloon in a tip portion of an insertion unit of an endoscope, but also provides a second balloon in a tip portion of an insertion aid (this is also called an over tube or a sliding tube). It is possible to make the insertion unit and insertion aid fix in an intestinal tract, such as a small intestine, by having the first balloon and second balloon expanded. Hence, by inserting the insertion unit and insertion aid by turns with repeating expansion and shrinkage of the first balloon and second balloon, it is possible to insert the insertion unit into the depth of a complicatedly bending intestinal tract, such as a small intestine.

SUMMARY OF THE INVENTION

By the way, in recent years, there has been a request of modifying a mounting location of a balloon, which is mounted on an insertion unit of an endoscope, according to an application. For example, when performing a bending operation of a bend of an insertion unit after expanding the balloon, it is desired to mount the balloon in a base end side further than in the bend. In addition, when it is desired to enlarge a stroke of the insertion operation mentioned above, or when it is desired to obtain a blurless observation image after expansion of a balloon, it is desired to mount the balloon near a tip of an insertion unit.

Nevertheless, in the endoscope disclosed in Japanese Patent Application Laid-Open No. 2005-334475, since an opening of an air supply passage to supply and suck air to/from the balloon on an outer peripheral surface of a tip portion of the insertion unit, it is only possible to mount the balloon in the vicinity of this opening.

A method in which a tube is post-installed, the tube being an air supply passage in an outside of an insertion unit is conceivable as a method of mounting a balloon in an arbitrary location. However, in this case, since a tip of the tube must be arranged inside the balloon, there arise problems of becoming difficult to fix the balloon, and being hard to keep airtightness after fixing the balloon.

The present invention was made in view of such a situation, and aims at providing an endoscope which can easily fix a balloon and keep airtightness after the fixation, and can raise a degree of freedom of a mounting location of the balloon.

In order to attain the above-mentioned object, an invention according to a first aspect is an endoscope apparatus which includes an insertion unit which is inserted into a body, and a pipeline which is provided inside the insertion unit, and supplies a fluid to a balloon which is mounted on an outer peripheral surface of the insertion unit, characterized in that the pipeline is made to have openings in a plurality of locations in an axial direction of the insertion unit on the outer peripheral surface of the insertion unit.

According to the invention described in the first aspect, since the pipeline is made to have openings in a plurality of locations in an axial direction of the insertion unit, it is possible to select an opening from the plurality of openings and to mount a balloon. That is, according to the invention described in the first aspect, it is possible to select a mounting position of a balloon in the axial direction of the insertion unit from two or more locations. In addition, according to the invention of the first aspect, since the pipeline is provided inside the insertion unit, it is possible to easily mount a balloon, and to keep securely airtightness between an outer peripheral surface of the insertion unit and an inner peripheral surface of the balloon.

An invention according to a second aspect is characterized in that each sealing device is mounted detachably in the plurality of openings in the invention according to the first aspect. As the each sealing device according to the second aspect, for example, there is a rubber ring which is fit outside on the insertion unit, a rubber plug pressed fit into the opening, a plug member fit to or screwed into the opening, an end of the balloon fixed in a location of the opening, or a valve member arranged in the pipeline.

An invention described in a third aspect is characterized in that at least one opening among the plurality of openings is provided in a fixed location of a balloon which is mounted so as to be made to communicate with another opening, in the invention according to the first or second aspects. According to the invention according to the third aspect, it is possible to seal the opening by a balloon which is mounted on another opening.

An invention according to a fourth aspect is characterized in that the opening is provided in a concave groove formed in an outer periphery of the insertion unit over a round, in the invention according to any one of the first to third aspects. According to the invention according to the fourth aspect, since the opening is provided in the concave groove, it is possible to arrange a rubber ring, which seals the opening, inside the concave groove, and hence, it is possible to prevent the rubber ring from projecting from an outer peripheral surface of the insertion unit. In addition, according to the invention according to the fourth aspect, since the opening is provided in the concave groove, it becomes hard for the opening to be sealed by the balloon when a fluid is sucked from the opening, and hence, it is possible to shrink the balloon securely.

An invention according to a fifth aspect is characterized in that the plurality of openings is provided in a tip side and a base end side of a bend respectively, which is formed in the insertion unit and is given a bending operation, in the invention according to any one of the first to fourth aspects.

According to the present invention, since a plurality of openings is provided in an axial direction of the insertion unit, it is possible to mount a balloon in two or more locations in the axial direction of the insertion unit. In addition, according to the present invention, since a pipeline is provided inside an insertion unit, it is possible to easily mount a balloon, and to keep securely airtightness between an outer peripheral surface of the insertion unit and an inner peripheral surface of the balloon.

DETAILED DESCRIPTION OF THE PREFERRED EMBODIMENTS

Preferable embodiments of an endoscope according to the present invention will be described in detail with reference to accompanying drawings.

Figure 1:
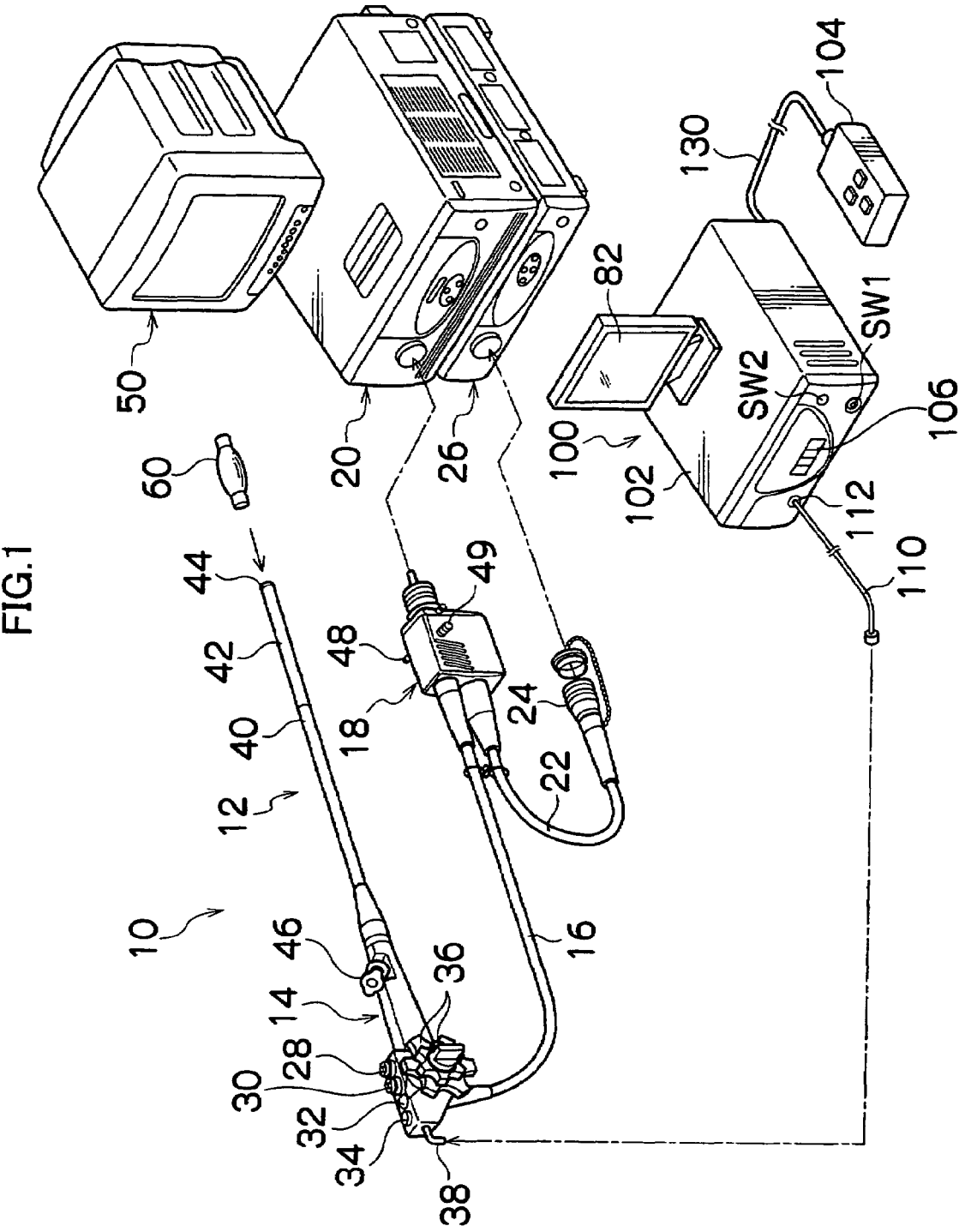
FIG. 1 is a system block diagram of an endoscope apparatus to which an endoscope which relates to the present invention is applied.

FIG. 1 is a system block diagram showing an example of an endoscope apparatus to which the endoscope which relates to the present invention is applied. As shown in FIG. 1, an endoscope apparatus mainly includes an endoscope 10 and a balloon controller 100.

The endoscope 10 includes a hand operation unit 14 and an insertion unit 12 which is installed in connection with this hand operation unit 14 and is inserted inside a living body. A universal cable 16 is connected to the hand operation unit 14, and an LG connector 18 is provided at a tip of this universal cable 16. The LG connector 18 is detachably connected to a light source apparatus 20, and thereby illumination light is transmitted to an illumination light optical system (not shown) provided at a tip of the insertion unit 12. In addition, an electric connector 24 is connected to the LG connector 18 through a cable 22, and this electric connector 24 is detachably connected to a processor 26.

In the hand operation unit 14, an air supply/water supply button 28, a suction button 30, a shutter release 32, and a function switching button 34 are juxtaposed, while a pair of angle knobs 36 and 36 are provided. A balloon air supply opening 38 is formed by an L-shaped bent pipe in a base end portion of the hand operation unit 14. A below-mentioned balloon 60 can be expanded or shrunk by supplying or sucking a fluid, such as air, to/from this balloon air supply opening 38.

The insertion unit 12 includes an elastic portion 40, a bending portion 42, and a tip portion 44 sequentially from a hand operation unit 14 side. The elastic portion 40 is a portion which has sufficient flexibility, and is installed in connection with a base end side of the bending portion 42.

The bending portion 42 is constructed so as to be bent remotely by rotating the angle knobs 36 and 36 of the hand operation unit 14. For example, the bending portion 42 is constructed so that the bending portion 42 may be given a bending operation by a plurality of cylindrical joint rings being coupled rotatably by a guide pin, a plurality of operation wires being made to be inserted inside the joint rings and being guided by the guide pin, and the operation wires being pushed and pulled. It is possible to orient the tip portion 44 in a desired direction by giving the bending operation to this bending portion 42.

Figure 2:
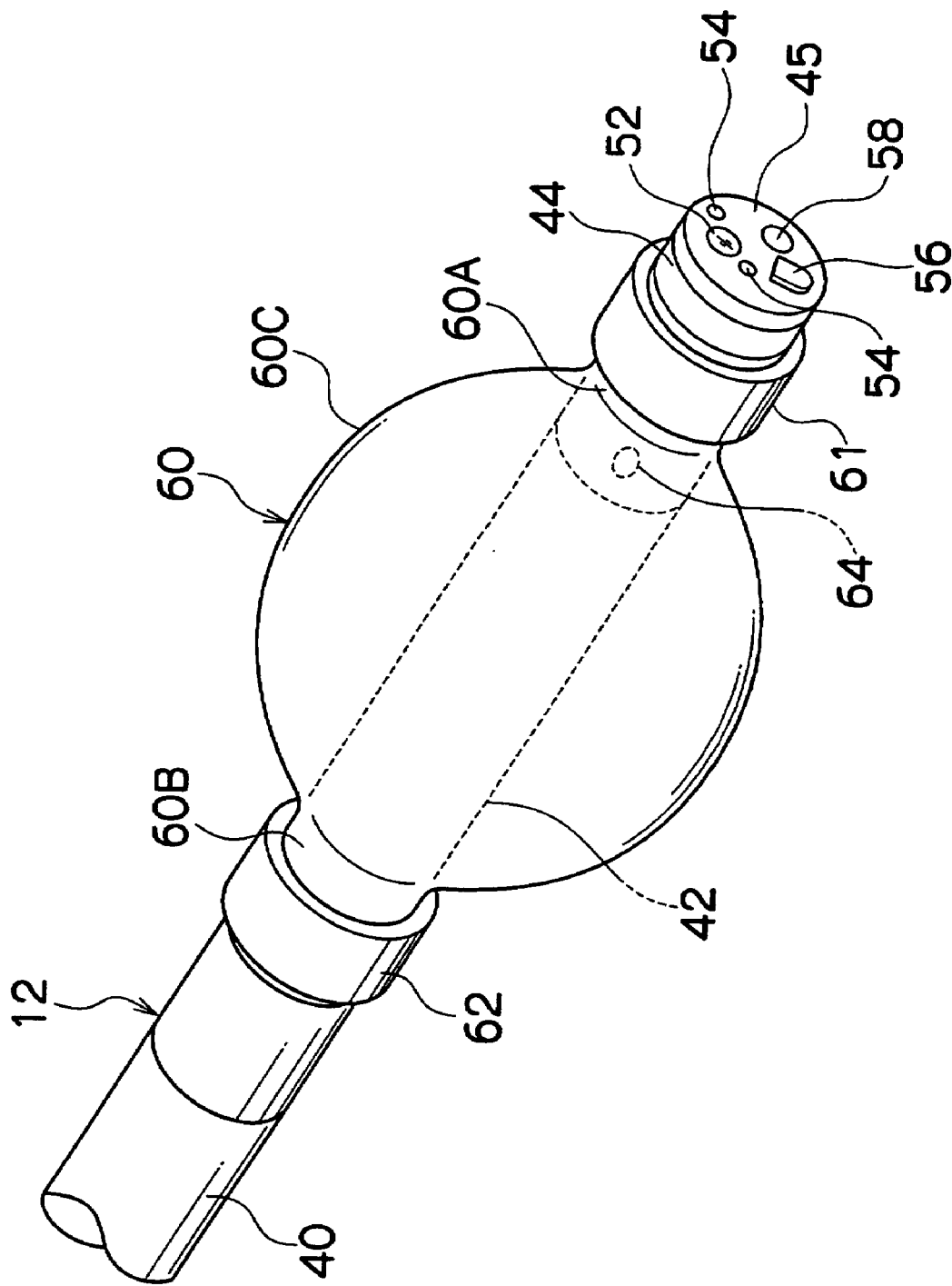
FIG. 2 is a perspective view showing a tip portion of an insertion unit.

The tip portion 44 is a hard portion provided at a tip of the insertion unit 12, and as shown in FIG. 2, an observation optical system 52, illumination light optical systems 54 and 54, an air supply/water supply nozzle 56, and a forceps opening 58 are provided in its tip surface 45. A CCD (not shown) is arranged behind the observation optical system 52, and a signal cable (not shown) is connected to a substrate which supports that CCD. The signal cable is inserted into the insertion unit 12, the hand operation unit 14, a universal cable 16, and the like, and is extended to an electric connector 24 to be connected to a processor 26. Therefore, an observation image taken in by the observation optical system 52 is imaged on a light-receiving surface of the CCD to be converted into an electric signal, and this electric signal is output to the processor 26 in FIG. 1 through the signal cable to be converted into a video signal. Thereby, the observation image is displayed on a monitor 50 connected to the processor 26.

An emission end of a light guide (not shown) is arranged behind the illumination light optical systems 54 and 54 in FIG. 2, the light guide is inserted into the insertion unit 12, hand operation unit 14, and universal cable 16 in FIG. 1, and its incident end is arranged inside the LG connector 18. Hence, by connecting the LG connector 18 to the light source apparatus 20, illumination light radiated from the light source apparatus 20 is transmitted to the illumination light optical systems 54 and 54 in FIG. 2 through the light guide, and is radiated forward from the illumination light optical systems 54 and 54.

The air supply/water supply nozzle 56 communicates with a valve (not shown) operated with the air supply/water supply button 28 in FIG. 1, and this valve communicates with an air supply/water supply connector 48 provided in the LG connector 18. An air supply/water supply device not shown is connected to the air supply/water supply connector 48, and air and water are supplied. Hence, it is possible to inject air or water from the air supply/water supply nozzle 56 to the observation optical system by operating the air supply/water supply button 28.

The forceps opening 58 in FIG. 2 communicates with a forceps insertion portion 46 in FIG. 1. Therefore, it is possible to draw a treatment tool from the forceps opening 58 by inserting the treatment tool, such as a forceps, from the forceps insertion portion 46. In addition, the forceps opening 58 communicates with a valve operated with the suction button 30, and this valve is connected to a suction connector 49 of the LG connector 18. Hence, it is possible to suck a pathological change portion or the like from the forceps opening 58 by connecting a not-shown suction device to the suction connector 49, and manipulating the valve with the suction button 30.

Figure 3:
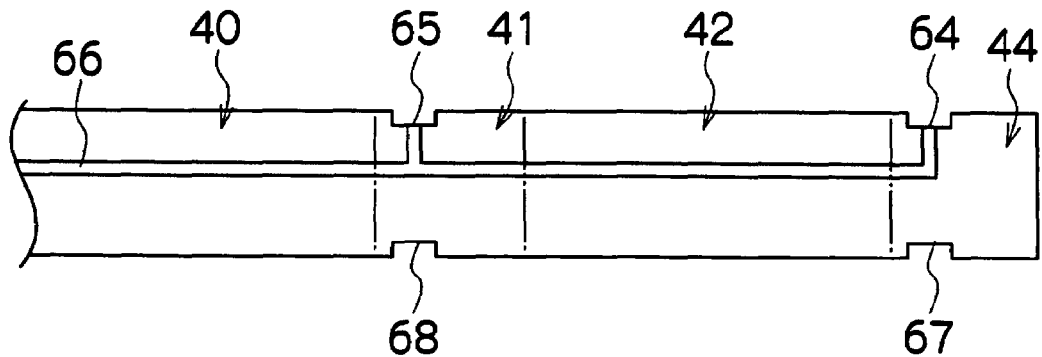
FIG. 3 is a pipeline diagram showing a pipeline in the insertion unit schematically.

FIG. 3 is a diagram showing a pipeline in the insertion unit 12 schematically. As shown in this diagram, a pipeline 66 is provided inside the insertion unit 12, this pipeline 66 is branched on the way, and two openings are provided in an outer peripheral surface of the insertion unit 12. That is, two openings 64 and 65 are provided in the outer peripheral surface of the insertion unit 12.

The opening 64 is provided in a concave groove 67 formed in a base end portion of the tip portion 44. The concave groove 67 is formed in an outer peripheral surface of the tip portion 44 over a round, and is formed in width of a rubber ring 69 shown in FIG. 5. Hence, when the rubber ring 69 is fit outside the concave groove 67, the rubber ring 69 is housed inside the concave groove 67.

The opening 65 is provided in a concave groove 68 formed in a base end portion of a connection ring 41 which connects the bending portion 42 and/with the elastic portion 40. The concave groove 68 is formed in an outer peripheral surface of the connection ring 41 over a round, and is formed in the same width as the above-mentioned concave groove 67, that is, in the width of the rubber ring 69 shown in FIG. 4. Hence, when the rubber ring 69 is fit outside the concave groove 68, the rubber ring 69 is contained inside the concave groove 68.

The rubber ring 69 is formed in a ring shape of an elasticity material such as rubber, and its inner diameter before outside fitting is formed a little smaller than outer diameters in locations of the concave grooves 67 and 68. Hence, by making the rubber ring 69 fit outside the concave groove 67 or 68, the rubber ring 69 sticks to a peripheral surface of the concave groove 67 or 68 by its own elastic force, and the opening 64 or 65 is sealed. In addition, although it is made to make the common rubber ring 69 fit outside the concave grooves 67 and 68 in this embodiment, it is not limited to this, but different rubber rings may be made to fit outside.

Figure 4:
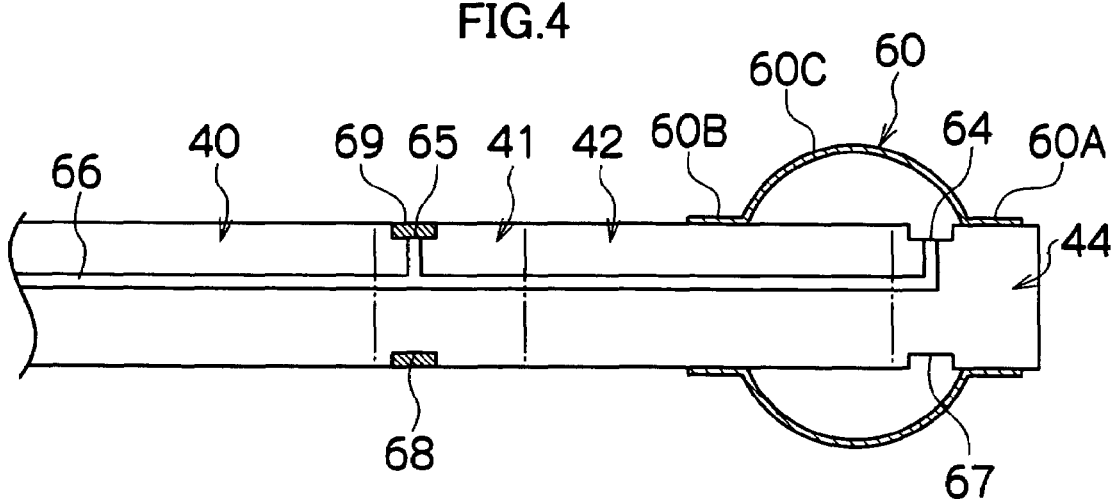
FIG. 4 is a pipeline diagram of the insertion unit where an opening in a tip side is selected and a balloon is mounted.
Figure 5:
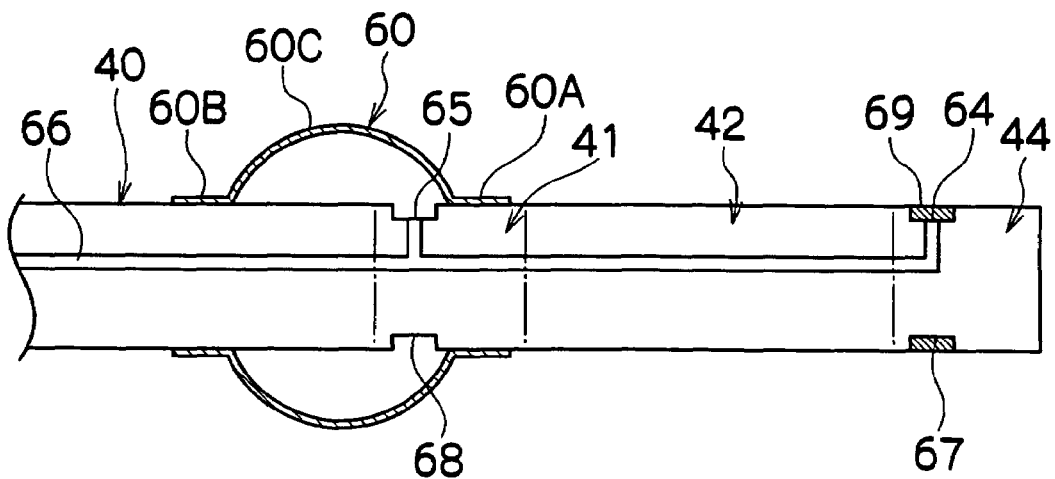
FIG. 5 is a pipeline diagram of the insertion unit where an opening in a base end side is selected and a balloon is mounted.

As shown in FIG. 4 or 5, the balloon 60 is mounted in a location of the opening 64 or 65. The balloon 60 is formed of an elastic material, such as rubber, in substantially cylindrical shape whose end portion is shrunk, and includes a tip portion 60A and a base end portion 60B with a smaller diameter, and a swelling portion 60C which is a central portion. After inserting the insertion unit 12 and arranging it in a predetermined location of the insertion unit 12, this balloon 60 is fixed to the insertion unit 12 by putting rings 61 and 62 (referring to FIG. 2), made of rubber, in the tip portion 60A and base end portion 60B. In addition, a fixing method of the tip portion 60A and base end portion 60B is not limited particularly, it is also sufficient to wind a string to fix them. In addition, the balloon 60 is constructed expandably, and it is made to be substantially spherical when it expands, and it sticks to an outer surface of the insertion unit 12 when it shrinks.

The above-mentioned pipeline 66 in FIG. 3 includes a tube, a pipe, a hole, and the like, and a base end side (left side in FIG. 3) of the pipeline 66 communicates with the balloon air supply opening 38 of the hand operation unit 14 in FIG. 1. The below-mentioned balloon controller 100 is connected to the balloon air supply opening 38 through a tube 110. Therefore, it is possible to supply and suck a fluid to/from the openings 64 and 65 by supplying and sucking a fluid, such as air, from the balloon controller 100.

The balloon controller 100 is an apparatus which not only supplies and sucks a fluid to the balloon 60 (refer to FIGS. 4 and 5) to expand and shrink the balloon 60, but also controls internal pressure of the balloon 60 at that time, and is mainly constructed by an apparatus main body 102 and a hand switch 104 for remote control.

A power switch SW1, a stop switch SW2, and a pressure display unit 106 are provided in a front face of the apparatus main body 102. The pressure display unit 106 is a panel which displays a pressure value of the balloon 60, and displays an error code at the time of occurrence of an abnormality such as a burst of a balloon.

The tube 110 which performs air supply and suction to/from the balloon 60 is connected to the front face of the apparatus main body 102. A backflow preventing unit 112 for preventing a backflow of humors when the balloon 60 is burst is provided in a junction between the tube 110 and apparatus main body 102. The backflow preventing unit 112 is constructed by incorporating a filter for gas-liquid separation into an inside of a hollow disk-like case (not shown) which is mounted detachably in the apparatus main body 102, and prevents a liquid with the filter from flowing into the apparatus main body 102.

On the other hand, various kinds of switches are provided in the hand switch 104. For example, a stop switch which is the same as the stop switch SW2 of the apparatus main body 102 side, an ON/OFF switch which indicates pressurization or depressurization of the balloon 60, a pause switch for holding pressure of the balloon 60, and the like are provided. This hand switch 104 is electrically connected to the apparatus main body 102 through a cord 130. In addition, although not shown in FIG. 1, a display unit which shows an air supply state or an exhaust state of the balloon 60 is provided in the hand switch 104.

The balloon controller 100 constructed as described above not only supplies air to the balloon 60 to expand it, but also to control the air pressure to a constant value to keep the balloon 60 in an expanding state. In addition, the balloon controller 100 not only sucks air from the balloon 60 to shrink it, but also to control the air pressure to a steady value to keep the balloon 60 in a shrinking state.

The balloon controller 100 is connected to a balloon-dedicated monitor 82, and makes a pressure value, and expansion and shrinkage states of the balloon 60 displayed on the balloon-dedicated monitor 82 when expanding and shrinking the balloon 60. In addition, the pressure value, and expansion and shrinkage states of the balloon 60 may be superimposed on an observation image of the endoscope 10 to be displayed on the monitor 50.

As an example of an operation method of the endoscope apparatus constructed as described above, the insertion unit 12 is inserted in a push mode, and a balloon 60 is expanded if necessary, and is fixed inside a living body (for example, large intestine). Then, after drawing the insertion unit 12 to simplify a pipe shape of the living body (for example, large intestine), the balloon 60 is shrunk and the insertion unit 12 is further inserted in the depth of an intestinal tract. For example, the insertion unit 12 is inserted from an anus of a subject, the insertion unit 12 is fixed to the intestinal tract by the balloon 60 being expanded when the tip of the insertion unit 12 passes over a sigmoid colon, and the insertion unit 12 is pulled for the sigmoid colon to be made substantially linear. Then, the balloon 60 is shrunk and the tip of the insertion unit 12 is being inserted in the depth of the intestinal tract. Thereby, it is possible to insert the insertion unit 12 into the depth of the intestinal tract.

Next, an operation of the endoscope 10 constructed as described above will be explained.

The endoscope 10 includes two openings 64 and 65 in the insertion unit 12, and a surgeon selects one of the two openings 64 and 65 to mount the balloon 60 according to an application. FIGS. 2 and 4 show examples of the balloon 60 being mounted in location of the opening 64, and FIG. 5 shows an example of the balloon 60 being mounted in a location of the opening 65.

As shown in FIGS. 2 and 4, when the balloon 60 is mounted in the location of the opening 64, the tip portion 60A of the balloon 60 is fixed on an outer peripheral surface of the tip portion 44 which is nearer to the tip than the opening 64, and the base end portion 60B of the balloon 60 is fixed on an outer peripheral surface of the bending portion 42. Thereby, since the opening 64 is arranged inside the swelling portion 60C of the balloon 60, it is possible to expand and shrink the balloon 60 by supplying and sucking a fluid, such as air, to/from the opening 64.

In this case, the rubber ring 69 is made to fit outside the concave groove 68, and the opening 65 which is not selected is sealed with the rubber ring 69. Thereby, when a fluid is supplied and sucked by the balloon controller 100, the fluid is supplied and sucked to/from the opening 64.

When the balloon 60 is mounted in the location of the opening 64 as described above, the balloon 60 is mounted near the tip of the insertion unit 12. Hence, since the observation optical system 52 of the tip portion 44 is fixed to the inside of the living body when the balloon 60 is expanded and the insertion unit 12 is fixed to the inside of the living body (large intestine or the like), it is possible to obtain an observation image with a small blur. In addition, since the balloon 60 is near the tip of the insertion unit 12, the insertion unit 12 can be fixed to the further depth of the living body when the balloon 60 is expanded and fixed to the inside of the living body. Hence, it is possible to enlarge a stroke in one insertion operation.

As shown in FIG. 5, when mounting the balloon 60 in a location of the opening 65, the tip portion 60A of the balloon 60 is fixed on an outer peripheral surface of the connection ring 41 which is nearer to the tip than the opening 65, and the base end portion 60B of the balloon 60 is fixed on an outer peripheral surface of the elastic portion 40. Thereby, since the opening 65 is arranged inside the swelling portion 60C of the balloon 60, it is possible to expand and shrink the balloon 60 by supplying and sucking a fluid, such as air, to/from the opening 65.

In this case, the rubber ring 69 is made to fit outside the concave groove 67, and the opening 65 which is not selected is sealed with the rubber ring 69. Thereby, when the fluid is supplied and sucked by the balloon controller 100, the fluid is supplied and sucked to and from the opening 65.

When the balloon 60 is mounted in the location of the opening 65 as described above, the balloon 60 is mounted in a base end side further than the bending portion 42. Hence, it is possible to perform a bending operation of the bending portion 42 freely in a state that the balloon 60 is expanded and the insertion unit 12 is fixed to the inside of the living body (large intestine or the like). Therefore, since it is possible to orient the tip portion 44 to a pathological change portion or the like in a state that the insertion unit 12 is fixed to the inside of the living body, this is suitable for making an endoscope treatment tool, such as a forceps, inserted into a forceps channel of the endoscope 10 to treat the pathological change portion or the like.

In this way, according to this embodiment, it is possible to select a mounting position of the balloon 60 according to an application of a balloon type endoscope. In addition, in the above-mentioned endoscope 10, since the pipeline 66 is provided in the insertion unit 12, differently from a case that the pipeline 66 is arranged outside the insertion unit 12, it is possible to mount the balloon 60 easily, and to secure airtightness between the balloon 60 and insertion unit 12.

In addition, in the endoscope 10 of this embodiment, since the openings 64 and 65 are provided in the concave grooves 67 and 68, when the rubber ring 69 is made to fit outside and seal the opening 64 or 65, it is possible to prevent the rubber ring 69 from projecting from an outer peripheral surface of the insertion unit 12. Furthermore, in this embodiment, since the openings 64 and 65 are provided in the concave grooves 67 and 68, it becomes hard for the opening 64 or 65 to be sealed by the balloon 60 when a fluid is sucked from the opening 64 or 65, and hence, it is possible to shrink the balloon 60 securely.

Furthermore, although the rubber ring 69 is used in the embodiment mentioned above as a sealing device which seals the opening 64 or 65 which is not selected, the sealing device is not limit to this, and may be just a device which seals the opening 64 or 65, or a branching portion of the pipeline 66. For example, it is also sufficient to press fit a rubber plug into the opening 64 or 65, or to seal the opening 64 or 65 by fitting or screwing a plug member into the opening 64 or 65. In addition, as mentioned later, it is also sufficient to seal the opening 64 or 65 using the tip portion 60A or base end portion 60B of the balloon 60. Furthermore, a pipeline-sealing device such as a solenoid valve may be provided in the branching portion of the pipeline 66.

In addition, although the example of providing the two openings 64 and 65 is explained in the embodiment mentioned above, the number of the openings is not limited to this, but three or more openings may be provided in an axial direction of the insertion unit 12. For example, an opening may be provided in an outer peripheral surface of the elastic portion 40 in addition to the openings 64 and 65 mentioned above.

Figure 6:
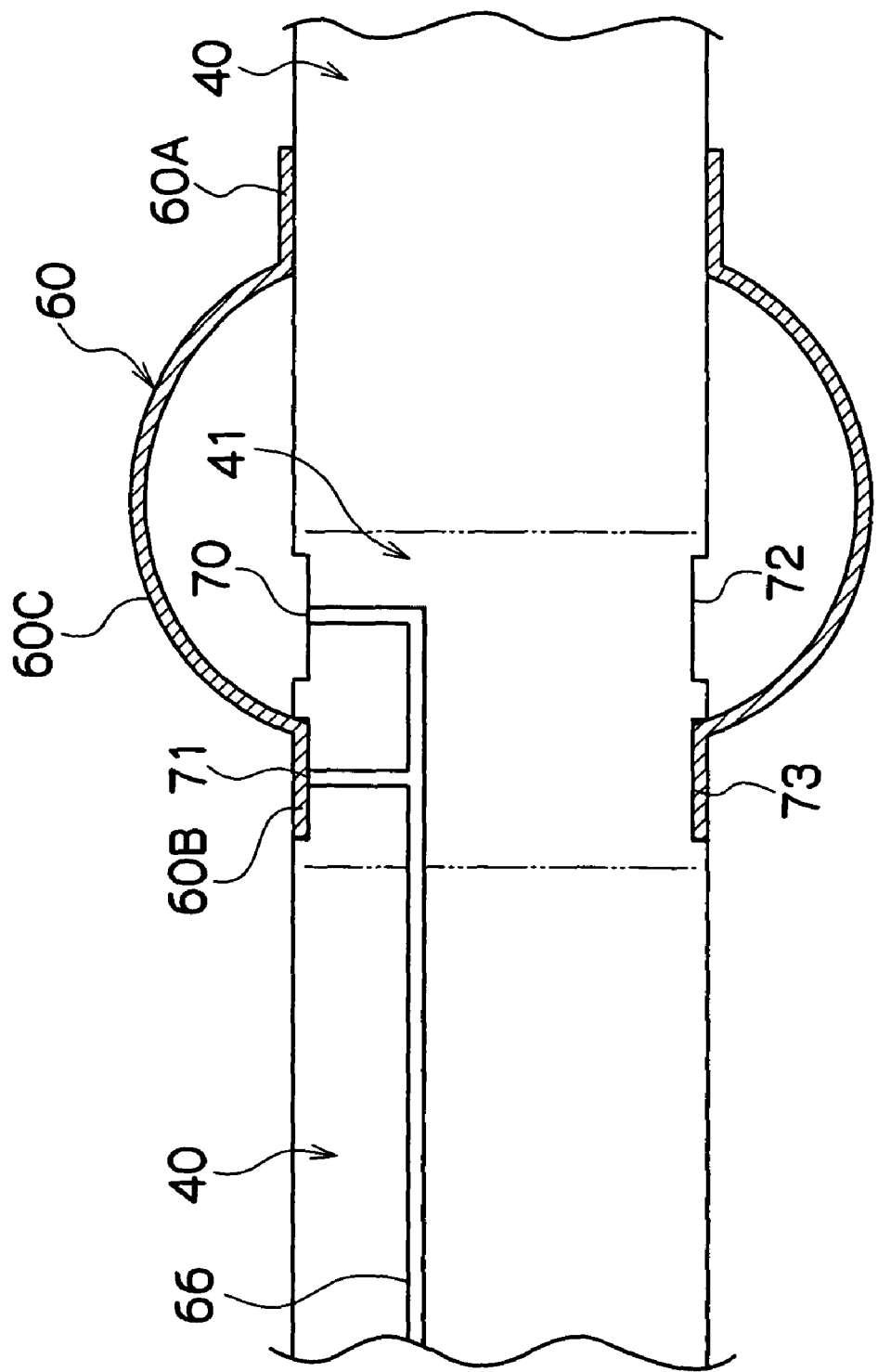
FIG. 6 is a pipeline diagram of the insertion unit where two opening are provided in a connection ring.
Figure 7:
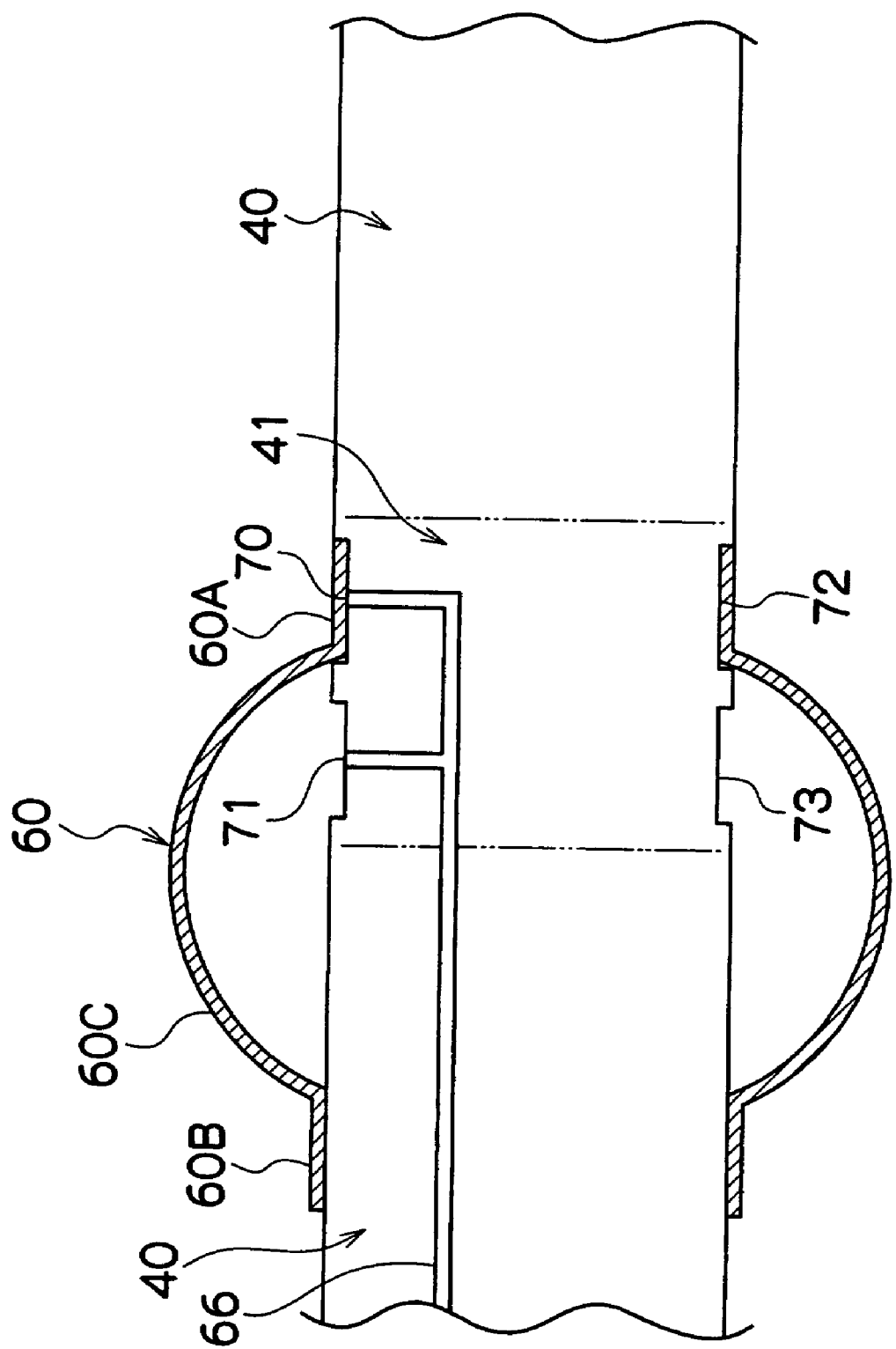
FIG. 7 is a pipeline diagram of the insertion unit where a mounting location of a balloon is different from that in FIG. 6.

Furthermore, although the opening 64 is provided in the tip portion 44 of the insertion unit 12 and the opening 65 is provided in the connection ring 41 in the embodiment mentioned above, locations of the openings are not limited to this, but what is necessary is just to be formed in different locations in the axial direction of the insertion unit 12. For example, as shown in FIGS. 6 and 7, openings 70 and 71 may be provided in the tip portion and base end portion of the connection ring 41, respectively. The openings 70 and 71 are provided in concave grooves 72 and 73 formed in the outer peripheral surface of the connection ring 41 over a round in a circumferential direction, respectively. Widths of the concave grooves 72 and 73 are formed in widths of the tip portion 60A and base end portion 60B of the balloon 60, respectively.

When the opening 70 is selected in the endoscope constructed as described above, as shown in FIG. 6, the tip portion 60A of the balloon 60 is fixed on the bending portion 42, and the base end portion 60B of the balloon 60 is fixed in a location of the concave groove 73. Hence, the opening 71 which is not selected is sealed by the base end portion 60B of the balloon 60.

In addition, when the opening 71 is selected, as shown in FIG. 7, the tip portion 60A of the balloon 60 is fixed by the concave groove 72, and the base end portion 60B of the balloon 60 is fixed by the elastic portion 40. Hence, the opening 70 which is not selected is sealed by the tip portion 60A of the balloon 60.

According to the endoscope constructed as described above, it is possible to select a mounting position of the balloon 60 from a tip portion side and a base end side of the connection ring 41. In addition, according to this embodiment, since the opening 70 or 71 which is not selected is sealed using the tip portion 60A or base end portion 60B of the balloon 60, it is not necessary to provide a sealing device separately. In addition, according to this embodiment, since the tip portion 60A or base end portion 60B of the balloon 60 after mounting are arranged inside the concave groove 72 or 73 by providing the openings 70 and 71 in the concave grooves 72 and 73, it is possible to prevent the tip portion 60A or base end portion 60B from projecting from an outer peripheral surface of the insertion unit 12.

Figure 8:
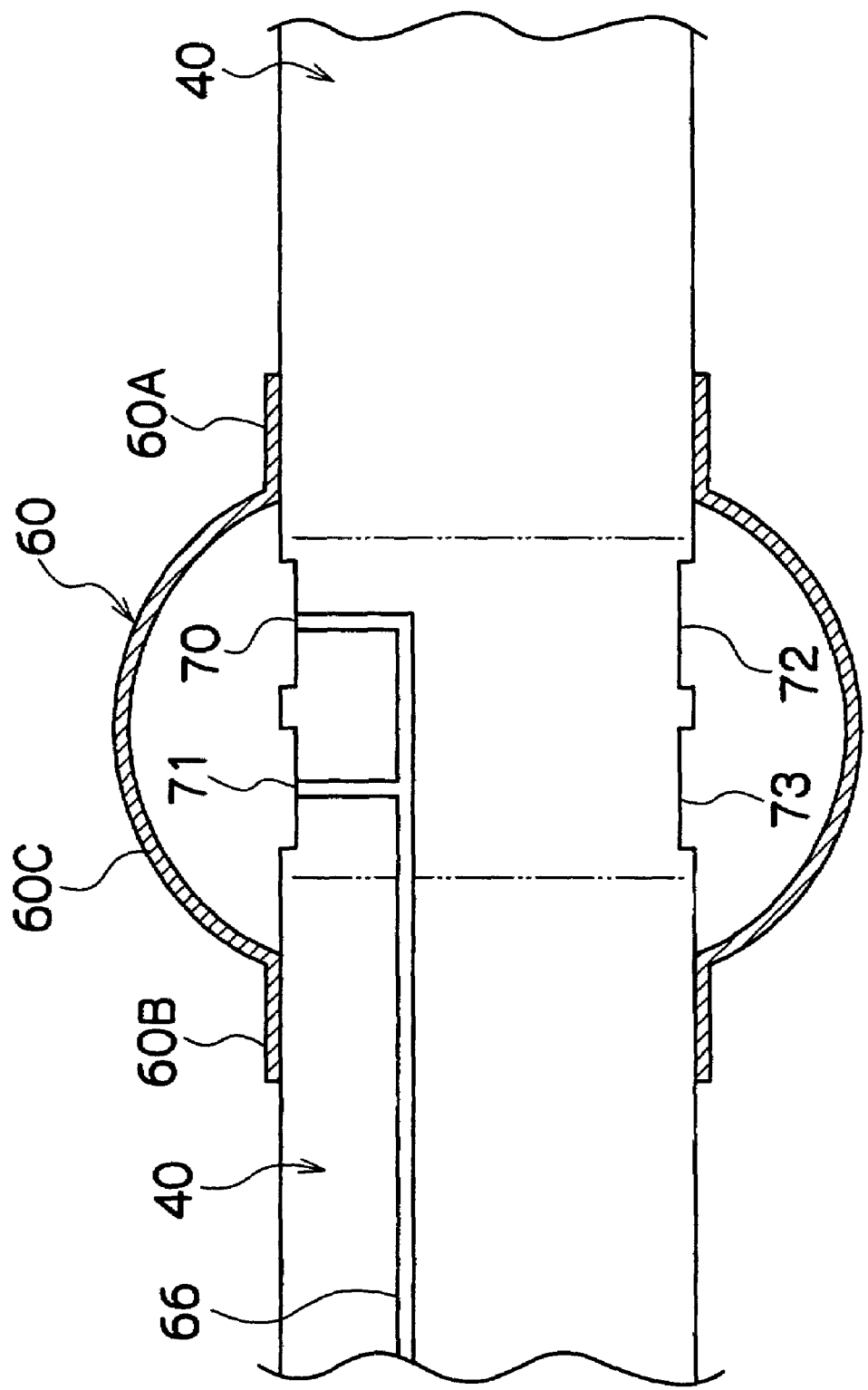
FIG. 8 is a pipeline diagram of the insertion unit where a mounting location of a balloon is different from that in FIG. 6.

Moreover, in the case of the above-mentioned endoscope, the balloon 60 may be mounted as shown in FIG. 8. That is, the tip portion 60A of the balloon 60 may be fixed in the tip side further than the concave groove 72, and the base end portion 60B may be fixed in the base end side further than the concave groove 73. Thereby, the two openings 70 and 71 are arranged inside the balloon 60, and supply and suction of a fluid are performed through the two openings 70 and 71. Hence, it is possible to prevent the balloon from expanding and shrinking with partially uneven.

In addition, although the pipeline 66 is branched and is made to communicate with the openings 64 and 65, or 70 and 71 in the embodiment mentioned above, the present invention is not limited to this, but an independent pipeline for each of the openings 64, 65, 70 and 71 may be provided, and may be connected to the balloon controller 100.

What is claimed is:

1. An endoscope comprising:
   an insertion unit which is to be inserted into a body;
   a balloon mounted on an outer peripheral surface of the insertion unit; and
   a pipeline provided inside the insertion unit for supplying a fluid to the mounted balloon,
   wherein a plurality of openings are provided in an axial direction of the insertion unit on the outer peripheral surface of the insertion unit and communicating with the pipeline for expanding the balloon,
   from the plurality of openings, at least one of a tip side opening located at a tip in the axial direction and a base end side opening located at a base end in the axial direction is closed by a cylindrical band integrally formed with the balloon at a tip portion or a base end portion of the balloon to prevent the fluid from leaking from the closed opening, and
   wherein, according to an application of said endoscope, one of the plurality of openings is selected and a mounting location of the balloon to the insertion unit is changed in accordance with the selected opening,
   the plurality of openings exist in a concave groove formed over an entire circumference of an outer peripheral surface of the insertion unit,
   a depth of the concave groove is substantially the same as a thickness of the balloon, and when the band is attached to the concave groove, a surface of the insertion unit and a surface of the balloon become substantially flush at a part of the concave groove where the band is attached, and
   when the fluid is fed through the pipeline, the fluid is supplied from openings other than the opening closed by the band, and the balloon is expanded by the fluid.

2. The endoscope according to claim 1, wherein
   the insertion unit comprises an elastic portion having flexibility, a bending portion that is configured to bend, and a connecting portion that connects the elastic portion and the bending portion, and
   the tip side opening or the base end side opening is provided at the connecting portion.

* * * * *